United States Patent

Gehret et al.

[11] Patent Number: 4,567,190
[45] Date of Patent: Jan. 28, 1986

[54] PESTICIDAL PHENYLHYDRAZONOPYRROLIDINES

[75] Inventors: Jean-Claude Gehret, Aesch; Walter Traber, Reinach, both of Switzerland

[73] Assignee: Ciba-Geigy Corporation, Ardsley, N.Y.

[21] Appl. No.: 622,826

[22] Filed: Jun. 21, 1984

[51] Int. Cl.[4] .................... C07D 401/12; A61K 31/44
[52] U.S. Cl. .................................. 514/343; 514/370; 514/426; 546/281; 548/412; 548/198
[58] Field of Search ................ 546/281; 548/412, 198; 424/263, 270, 274; 514/343, 370, 426

[56] References Cited

FOREIGN PATENT DOCUMENTS 3035822 4/1981 Fed. Rep. of Germany .

Primary Examiner—Jane T. Fan
Attorney, Agent, or Firm—Edward McC. Roberts

[57] ABSTRACT

Substituted phenylhydrazonopyrrolidine derivatives of the formula

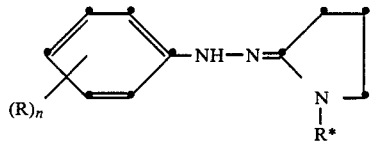

wherein
R is halogen or $C_1$–$C_4$-alkyl,
n is zero, 1 or 2, and
$R^*$ is the group —CH=N—$R_1$ or

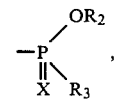

in which
$R_1$ is a pyridine group which is bound by way of a carbon atom, and which is unsubstituted or substituted by a methyl group, or is a 2-thiazolyl group, and
$R_2$ is methyl or ethyl,
$R_3$ is $C_1$–$C_4$-alkyl, $C_1$–$C_2$-alkoxy or $C_1$–$C_4$-alkylthio, and
X is oxygen or sulfur,
have valuable properties for controlling pests, such as phytoparasitic and zooparasitic insects and acarids, including in particular ectoparasites.

10 Claims, No Drawings

PESTICIDAL PHENYLHYDRAZONOPYRROLIDINES

The present invention relates to novel substituted phenylhydrazonopyrrolidine compounds, to processes for producing them, to compositions containing these compounds as active ingredients, and to the use of these compounds for controlling pests, particularly phytoparasitic and zooparasitic insects, and members of the order Acarina, including especially ectoparasites, for example mites and in particular ticks.

In the German Offenlegungsschrift No. 3,035,822, phenylhydrazinopyrroline compounds are described and their use for controlling mites suggested. These substances however can only partially satisfy the demands made of them in practice.

The novel compounds correspond to the general formula I

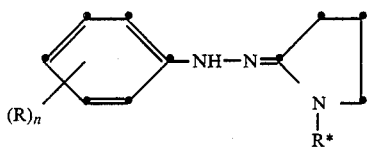

(I)

wherein
R is halogen or $C_1$-$C_4$-alkyl,
n is zero, 1 or 2,
R* is the group -CH=N-$R_1$ or

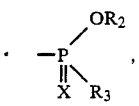

in which
$R_1$ is a pyridine group which is bound by way of a carbon atom, and which is unsubstituted or substituted by a methyl group, or is a 2-thiazolyl group, and
$R_2$ is methyl or ethyl,
$R_3$ is $C_1$-$C_4$-alkyl, $C_1$-$C_2$-alkoxy or $C_1$-$C_4$-alkylthio, and
X is oxygen or sulfur,
and the invention relates also to the acid addition salts of these compounds.

Depending on the meaning of the substituent R*, there are therefore embraced either amidine derivatives or (thio)phosphoryl derivatives of the formula I.

Examples of salt-forming acids are inorganic acids: hydrohalic acids, such as hydrofluoric acid, hydrochloric acid, hydrobromic acid or hydriodic acid, as well as sulfuric acid, phosphoric acid, phosphorous acid and nitric acid; and organic acids, such as acetic acid, trifluoroacetic acid, trichloroacetic acid, propionic acid, tartaric acid, formic acid, oxalic acid, succinic acid, maleic acid, lactic acid, glycolic acid, aconitic acid, citric acid, benzoic acid, benzenesulfonic acid, p-toluenesulfonic acid or methanesulfonic acid.

Halogen in the case of R is for example: fluorine, chlorine, bromine or iodine. Alkyl as substituent or part-substituent denoted by $R_3$ embraces methyl and ethyl and the isomers of propyl and butyl. $C_1$-$C_2$-Alkoxy as $R_3$ is methoxy and ethoxy.

Preferred compounds of the formula I wherein R* is the group -CH=N-$R_1$ (compound group Ia) are those in which R is chlorine and/or methyl, and n is 1 or 2, whilst $R_1$ has the meanings defined under the formula I. Particularly advantageous among the preferred compounds are those in which $R_{(n)}$ is 2,3-dichloro.

Individual compounds which are especially preferred are compounds Nos. 2a and 3a mentioned in the following (Table I).

Of the compounds of the formula I, the amidines of the formula Ia

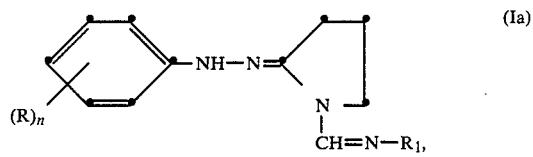

(Ia)

wherein R, $R_1$ and n have the meanings defined under the formula I, are produced by reacting a compound of the formula IIa with a compound of the formula IIIa

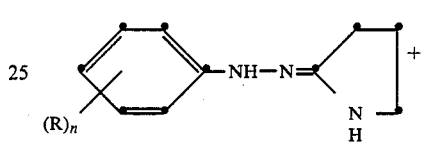

(IIa)

$$R_2-O-CH=N-R_1 \longrightarrow Ia$$

(IIIa)

wherein R, $R_1$ and n have the aforementioned meanings, and $R_2$ is a methyl or ethyl group.

The process is performed in a solvent or diluent inert to the reactants, and at a temperature of $-10°$ C. to $100°$ C., preferably between $10°$ and $60°$ C.

Of the compounds of the formula I, the compounds of the formula Ib in which R* is the group —P(X-)($OR_2$)$R_3$ as defined above

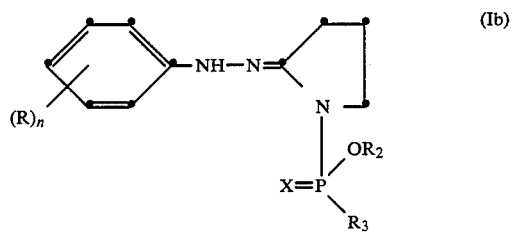

(Ib)

are produced by reacting a compound of the formula IIb with a compound of the formula IIIb

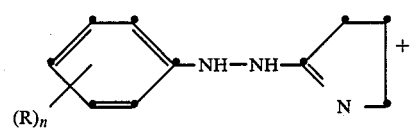

(IIb)

-continued

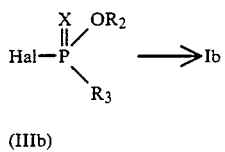

(IIIb)

wherein R, $R_2$, $R_3$, X and n have the meanings defined under the formula I, and Hal is a halogen atom, in particular a chlorine or bromine atom.

The process is performed in the presence of a base and of a solvent or diluent inert to the reactants, at a temperature of −30° to 100° C., preferably between −10° and 60° C.

Suitable solvents or diluents to be used in the aforementioned processes are for example: ethers and ethereal compounds, such as diethyl ether, diisopropyl ether, dioxane and tetrahydrofuran; also aromatic hydrocarbons, such as benzene, toluene and the xylenes, as well as ketones, such as acetone, methyl ethyl ketone and cyclohexanone. There can also be used for this purpose acetonitrile, and chlorinated hydrocarbons, such as dichloromethane, methylene chloride, carbon tetrachloride or chlorobenzene.

Bases that can be used are for example the following: alkali metal hydroxides, such as sodium or potassium hydroxide, or alkylamines, such as triethylamine or diisopropylethylamine, as well as pyridine or N-methylpyrrolidone.

The compounds of the formula I produced in the manner described can be converted into their acid salts by methods known per se.

The compounds of the formula I according to the invention or the compositions containing them as active ingredients are, surprisingly, distinguished in the field of pest control by particularly good biological activity and a favourable range of action. Furthermore, they have an unexpectedly high level of stability, such as is required for example with continuous use in soiled aqueous cattle dips. Compounds of the formula I and particularly those of the formula Ia have a surprisingly high tolerance to warm-blooded animals, a feature which greatly simplifies the handling of these compounds in practice.

The activity of the active substances is directed both against phytoparastic pests and against zooparasitic pests. Included amongst the plant pests are insects of the orders: Lepidoptera, Coleoptera, Homoptera, Heteroptera, Diptera, Thysanoptera, Anoplura, Siphonaptera, Mallophaga, Thysanura, Isoptera, Psocoptera and Hymenoptera.

The compounds of the formula I are also suitable for controlling members of the order Acarina of the families: Ixodidae, Argasidae, Tetranychidae and Dermanyssidae. The compounds of the formula I can be successfully used in particular for controlling phytopathogenic mites, for example of the families: Tetranychidae and Phytoptipalpidae (red spider mites), Tarsonemidae (thread foot mites) and Eriophydae (gall mites).

Besides their action against mosquitoes and flies, for example *Aedes aegypti* and *Musca domestica,* compounds of the formula I also have a favourable action for use in controlling insects that damage plants by eating, in crops of ornamental plants and productive plants, in particular in cotton crops (for example against *Spodoptera littoralis* and *Heliothis virescens*), as well as in cereal, fruit and vegetable crops (for example against *Laspeyresia pomonella, Leptinotarsa decemlineata* and *Epilachna varivestis*). The compounds of the formula I are distinguished also by a good action against larval insect stages and nymphs, especially of eating insect pests. The compounds according to the invention are suitable moreover for controlling soil insects (for example *Aulacophora femoralis, Chortophila brassicae, Diabrotica balteata, Pachnoda savigni* and *Scotia ypsilon*).

In particular, the compounds of the formula I can be used with great success against cicadas which damage plants, especially in rice crops, the compounds exhibiting both a systemic action and a contact action, for example against *Nilaparvata lugens* and *Laodelphax striatellus.*

The compounds of the invention are particularly highly effective against ticks (Ixodidae) parasitic on productive animals, especially against the species: Rhipicephalus, Amblyomma and Boophilus, and also against mites, for example *Dermanyssus gallinae,* and mange mites, for example: *Psoroptes ovis, Psoroptes bovis* and *Chorioptes bovis.*

The activity of the compounds of the formula I is directed also against further ectoparasites of the order Diptera, for instance of the families: Culicidae, Simuliidae, Tipulidae, Muscidae and Calliphoridae. In this respect, the active substances are particularly well suited for controlling Calliphoridae, for example *Lucilia sericata* (blowfly) and *Lucilia cuprina.*

Furthermore, members of the orders Aphaniptera (for example blood-sucking fleas) and Phthiraptera (for example blood-sucking lice) can be effectively controlled by use of the compounds of the formula I.

In their activity, the compounds according to the invention exhibit a spectrum which embraces all stages of development of the parasites, and beyond that also the oviposition of fertile eggs.

The control of the stated parasites is effected for example on the following domestic and productive animals: cattle, sheep, horses, red deer, poultry, goats, cats and dogs.

The higher stability of the compounds according to the invention ensures a duration of action which covers with respect to time the development cycles of several generations of parasites, so that, depending on the mode of application, for example in the case of productive animals, a single treatment per season is sufficient.

By virtue of their properties, the compounds of the formula I are very suitable for controlling ectoparasitic acarids and insects, for example by the direct treatment of animals, livestock housing and pastureland.

The action of the compounds according to the invention or of the compositions containing them can be considerably broadened and adapted to suit given conditions by the addition of other insecticides and/or acaricides. Suitable additives are for example representatives of the following classes of active substances: organic phosphorus compounds, nitrophenols and derivatives thereof, ureas, carbamates or chlorinated hydrocarbons.

For the control of pests, the compounds of the formula I according to the invention are used either alone or in the form of compositions, which additionally contain suitable carriers and/or additives, or mixtures of such substances. Suitable carriers and formulation auxiliaries can be solid or liquid and they correspond to the substances customarily used in formulation practice, for example natural or regenerated substances, solvents, dispersing agents, wetting agents, adhesives, thickeners or binders.

The formulations, that is to say, the compositions or preparations containing the active ingredient of the formula I, or combinations of these active ingredients with other insecticides or acaricides, and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane, paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil, or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite, and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I, or of the combinations of these active ingredients with other insecticides or acaricides, to be formulated: nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-taurine salts, as well as modified and unmodified phospholipides.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain in general an alkyl group having 8 to 22 C. atoms.

Examples of nonionic tensides which may be mentioned are: nonylphenolpolyethoxyethanols, castor oil-polyglycol ether, polypropylenepolyethylene oxide adducts, tributylphenoxypolyethoxyethanol, polyethylene glycol and octylphenoxypolyethoxyethanol. Also suitable are fatty acid esters of polyoxyethylene sorbitan, such as polyoxyethylene sorbitan trioleate.

In the case of the cationic tensides, they are in particular quaternary ammonium salts which contain as N-substituents at least one alkyl group having 8 to 22 C. atoms and, as further substituents, lower, optionally halogenated alkyl, benzyl or lower hydroxyalkyl groups. These salts are preferably in the form of halides, methyl sulfates or ethyl sulfates, for example stearyl-trimethylammonium chloride or benzyl-di-(2-chloroethyl)-ethylammonium bromide.

The tensides customarily used in formulation practice are described, inter alia, in the following publication:
"Mc Cutcheon's Detergents and Emulsifiers Annual", MC Publishing Corp., Ridgewood, N.J. 1982.

The pesticidal preparations contain as a rule 0.1 to 99%, particularly 0.1 to 95%, of active ingredient of the formula I, or of combinations of these active ingredients with other insecticides or acaricides; 1 to 99.9% of a solid or liquid additive; and 0 to 25%, especially 0.1 to 20%, of a tenside. Whereas commercial products are preferably in the form of concentrated compositions, the end-user employs as a rule diluted preparations containing 0.001-1% of active ingredient.

The compositions according to the invention are produced, in a manner known per se, by the intimate mixing and/or grinding of active ingredients of the formula I with suitable carriers, optionally with the addition of dispersing agents and solvents which are inert to the active ingredients.

The compositions can contain further additives, such as stabilisers, antifoaming agents, viscosity regulators, binders, adhesives and phospholipides, or other active ingredients for obtaining special effects.

Depending on the purpose and aim of the application, the compounds of the formula I or the compositions containing them are applied for example by spraying, for example in spray races, by dipping, for example in cattle dips, by the pour-on method, by washing, for example by the animal dressing procedure, and also by atomising, dusting, scattering or pouring.

EXAMPLE 1

Production of N-(2-[N'-(2',3'-dichlorophenylhydrazono)pyrrolidin-1-yl]-methylidene)-N-(6-methylpyridin-2-yl)amine [compound No. 1a]

A solution of 65.6 g (0.4 mol) of N-(6-methylpyridin-2-yl)-formiminoethyl ether in 100 ml of toluene is slowly added dropwise at about 25° C., with vigorous stirring, to 98 g (0.4 mol) of 2-[N'-(2',3'-dichlorophenylhydrazino)]pyrroline dissolved in 900 ml of toluene. The reaction mixture is subsequently stirred for 48 hours at about 45° C. until the reaction is completed; the mixture is then filtered and the filtrate is codcentrated by evaporation. After the addition of about 300 ml of diethyl ether, a yellow final product crystallises out; yield: 100 g (=68% of theory); melting point 150°-152° C.

EXAMPLE 2

Production of N-(2-[N'-(2',3'-dichlorophenylhydrazono)pyrrolidin-1-yl)]-methylidene-N-(3-methylpyridin-2-yl)amine [compound No. 2a]

To 9.8 g (0.04 mol) of 2-[N'-(2',3'-dichlorophenylhydrazino)]-pyrroline, dissolved in 90 ml of toluene, is slowly added dropwise at 20°-26° C., with vigorous stirring, a solution of 6.6 g (0.04 mol) of N-(3-methyl-pyridin-2-yl)formiminoethyl ether in 60 ml of toluene. The reaction mixture is subsequently stirred for 12 hours at about 45° C. until the reaction has finished; the mixture is then filtered and the filtrate is concentrated by evaporation. After the addition of about 50 ml of diethyl ether, a yellow final product crystallises out; yield: 7.3 g (=50.3% of theory); melting point: 155°–158° C.

EXAMPLE 3

Production of 1-(O-ethyl-S-n-propyl-thiophosphinyl)-2-[N'-(2',3'-dichlorophenylhydrazono)]-pyrrolidine [compound No. 1b]

To 14.6 g (0.06 mol) of 2-[N'-(2',3'-dichlorophenylhydrazino)]-pyrroline, dissolved in 50 ml of tetrahydrofuran, are added 7.6 g (0.075 mol) of triethylamine in 80 ml of toluene. There is then slowly added dropwise at 0°–5° C., with continuous stirring, a solution of 13.1 g (0.06 mol) of O-ethyl-S-n-propylthiochlorophosphate in 80 ml of toluene. Stirring is subsequently maintained for 24 hours at about 50° C. until the reaction has finished; the reaction mixture is filtered, the filtrate is concentrated by evaporation and afterwards chromatographed through aluminium oxide with a diethyl ether/hexane mixture (1:1 v/v). There is thus obtained a colourless final product; yield 11.5 g (=45% of theory); melting point: 91°–93° C.

The following compounds of the formula I are produced in a manner analogous to that described in the Examples given in the foregoing:

TABLE I (Structure: R'-, R''-, R'''-substituted phenyl–NH–N=⟨pyrrolidine ring with N–CH=N–R$_1$⟩)

| No. | R' | R'' | R''' | R$_1$ | m.p. [°C.] |
|---|---|---|---|---|---|
| 1a | H | Cl | Cl | 4-methylpyridin-2-yl (CH$_3$ at position para to N) | 150–152 |
| 2a | H | Cl | Cl | 3-methylpyridin-2-yl | 155–158 |
| 3a | H | Cl | Cl | thiazole | 137–139 |
| 4a | H | H | Cl | thiazole | 122–124 |

TABLE I-continued

| No. | R' | R'' | R''' | R$_1$ | m.p. [°C.] |
|---|---|---|---|---|---|
| 5a | Cl | Cl | H | 4-methylpyridin-2-yl | 167–169 |
| 6a | Cl | Cl | H | 3-methylpyridin-2-yl | 179–180 |
| 7a | H | Cl | Cl | pyridin-2-yl | 164–167 |
| 8a | H | Cl | Cl | pyridin-2-yl | |
| 9a | H | Cl | Cl | pyridin-2-yl | |

TABLE II (Structure: 2,3-dichlorophenyl–NH–N=⟨pyrrolidine ring with N–P(=X)(OR$_2$)(R$_3$)⟩)

| No. | R$_2$ | R$_3$ | X | m.p. [°C.] |
|---|---|---|---|---|
| 1b | C$_2$H$_5$ | SC$_3$H$_{7(n)}$ | S | 91–93 |
| 2b | C$_2$H$_5$ | C$_2$H$_5$ | S | 79–81 |
| 3b | C$_2$H$_5$ | SC$_4$H$_{9(i)}$ | O | |
| 4b | C$_2$H$_5$ | OC$_2$H$_5$ | O | |
| 5b | CH$_3$ | OCH$_3$ | O | |
| 6b | C$_2$H$_5$ | SC$_3$H$_{7(n)}$ | O | |

EXAMPLE 4

Action Against Ticks: Killing Action in Various Stages of Development

The test objects used are larvae (in each case about 50 and nymphs (in each case about 25) of the tick species *Amblyomma hebraeum* and *Boophilus microplus*, respectively. The test organisms are immersed for a short time in aqueous emulsions or solutions of the salts of the substances to be tested at a specific concentration. The emulsions or solutions in the small test tubes are absorbed with cotton wool and the wetted test insects are then left in the contaminated test tubes. An evaluation with respect to larvae is made after 3 days and with respect to nymphs and imagines after 14 days. There is determined the minimum substance concentration which results in a 100% mortality rate, expressed in ppm of active substance, relative to the total amount of emulsion or solution.

The compounds from Tables I and II result in a complete killing (100% mortality rate) at an application concentration of 25 ppm, the compounds Nos. 1a, 2a, 3a and 6a as well as the compounds Nos. 1b and 2b producing this result at a concentration as low as 12.5 ppm. This activity is retained by solutions of the compounds Nos. 2a and 3a, respectively, even after a period of several weeks.

EXAMPLE 5

Action Against Ticks: Inhibition of Oviposition

The test insects used are engorged females of the cattle tick *Boophilus microplus*. There are treated per concentration 10 ticks of an OP-resistant strain (for example Biarra strain) and 10 ticks of a normally sensitive strain (for example Yeerongpilly strain). The ticks are fixed on plates covered with double adhesive tape, and are then either wetted with aqueous emulsions or with solutions of the salts of the compounds to be tested, or brought into contact with a cotton-wool pad soaked with these liquids, and are subsequently kept in an air-conditioned chamber under constant conditions. An evaluation is made after three weeks, and the overall inhibition of the oviposition of fertile eggs is determined.

The inhibitory effect of the substances is expressed in terms of the minimum substance concentration in ppm to produce a 100% effect against normally sensitive adult female ticks and resistant adult female ticks, respectively. The compounds from Tables I and II effect a complete killing in the above test at a concentration of 25 ppm.

EXAMPLE 6

Action Against Phytoparasitic Insects

Cotton plants are sprayed with test solutions containing 25, 50 and 100 ppm, respectively, of the compound to be tested.

After the drying of the moist coating, *Spodoptera littoralis* larvae ($L_3$) are settled onto the cotton plants. The test is carried out at 24° C. with 60% relative humidity.

The compounds from the Tables I and II exhibit a good stomach-poison action against Spodoptera larvae, the compounds Nos. 1a–3a effecting complete killing at an applied concentration of 50 ppm, and the compounds of Table II a killing rate of over 90% at a concentration of 25 ppm.

EXAMPLE 7

Action Against *Lucilia Sericata* ($L_1$)

The test organisms used are freshly emerged larvae $L_1$. 1 ml of an aqueous suspension or solution of the active ingredient, the active-ingredient content being 1000 ppm, is mixed with a special larval culture medium at 50° C. in such a manner that a homogeneous mixture of 250 ppm of active ingredient is obtained. About 30 Lucilia larvae are used per test. The mortality rate is determined after four days.

The compounds in Table I effect a mortality rate of over 90%, and the compounds in Table II a mortality rate of over 80%. The compounds Nos. 1, 2 and 3 of Table I result in a complete killing of the larvae.

EXAMPLE 8

Action Against *Nilaparvata Lugens* (nymphs)

The test is carried out on growing plants. There are used in each case 4 rice plants (thickness of stem 8 mm) about 20 cm in height in pots (diameter 8 cm). The plants are sprayed, on a rotary plate, with in each case 100 ml of an acetonic solution containing 100, 200, 300 and 400 ppm, respectively, of active ingredient. After the drying of the applied coating, each plant is infested with 20 nymphs of the test insects in the third stage. In order to prevent the cicadas from escaping, a glass cylinder is placed over each of the infested plants and is covered with a gauze lid. The nymphs are kept on the treated plants over a period of 10 days until the following development stage is reached. An evaluation of the % mortality rate is made 1, 4 and 8 days after the treatment.

Compounds of Tables I and II exhibit a good action in the above test. A mortality rate of 80% is effected by the compound No. 1a at an applied concentration of 100 ppm and by the compound No. 2a at an applied concentration of 400 ppm.

EXAMPLE 9

Action Against Soil Insects (*Diabrotica Balteata*)

350 ml of soil (consisting of 95% by volume of sand and 5% by volume of peat) are mixed in each case with 150 ml of the respective aqueous emulsion preparation, the preparations containing the active ingredient to be tested in increasing concentration levels from 3 ppm to 400 ppm. Plastic beakers having an upper diameter of 10 cm are then partially filled with the treated soil. Into each beaker are placed ten Diabrotica balteata larvae in the third larval stage; four maize seedlings are then planted in each beaker and the beakers are topped up with soil. The filled beakers are covered over with plastic foil and kept at a temperature of about 22° C. Ten days after commencement of the test, the soil contained in the beakers is sieved, and the larvae remaining are examined with respect to the mortality rate.

Compounds from Tables I and II exhibit in this test a good action in that a mortality rate exceeding 80% is effected by the compound No. 1a at an applied concentration of 12.5 ppm, and by compound No. 2a at a concentration of 400 ppm.

Results similar to those given in the above Examples 3 to 9 can be obtained with active ingredients from the Tables I and II also with application over a longer period of time under practical conditions, without additional measures being carried out to stabilise the pH value of the preparations being applied.

EXAMPLE 10

Emulsion Concentrate 20 parts by weight of active ingredient are dissolved in 70 parts by weight of xylene, and to the solution are added 10 parts by weight of an emulsifier consisting of a mixture of tributylphenylpolyethylene glycol ether and the calcium salt of dodecylbenzenesulfonic acid.

A milky emulsion can be prepared by adding water in any desired proportion to the above emulsion concentrate.

EXAMPLE 11

Wettable Powder 5 to 30 parts by weight of active ingredient are vigorously mixed, in a mixing apparatus, with 5 parts by weight of an absorbent carrier (for example highly dispersed silicic acid) and 55 to 80 parts by weight of a carrier [bolus alba or kaolin]and a dispersing agent mixture consisting of 5 parts by weight of sodium lauryl sulfonate and 5 parts by weight of octylphenolpolyethylene glycol.

This mixture is ground in a dowelled disk mill or air jet mill to a particle size of 5-15 μm. The wettable powder thus obtained gives a good suspension in water.

EXAMPLE 12

Dust 5 parts by weight of finely ground active ingredient are thoroughly mixed with 2 parts by weight of a precipitated silicic acid, and 93 parts by weight of talcum.

EXAMPLE 13

Pour-on solution

| active substance | 30.0 g |
|---|---|
| sodium dioctylsulfosuccinate | 3.0 g |
| benzyl alcohol | 48.0 g |
| peanut oil | 19.8 g |
| | 100.8 g = 100 ml |

The active ingredient is dissolved with stirring in the benzyl alcohol, if necessary with gentle heating. To the solution are then added the sodium dioctylsulfosuccinate and the peanut oil, and these are dissolved with heating and thorough stirring.

EXAMPLE 14

Dressing Solution

| active ingredient | 30.00 g |
|---|---|
| sodium dioctylsulfosuccinate | 3.00 g |
| benzyl alcohol | 35.46 g |
| ethylene glycol monomethyl ether | 35.46 g |
| | 103.92 g = 100 ml |

The active ingredient is dissolved in the major portion of the mixture of the two solvents with vigorous stirring. The sodium dioctylsulfosuccinate is subsequently dissolved, if necessary with heating, and is finally added to the other constituents forming the mixture.

What is claimed is:

1. A substituted phenylhydrazonopyrrolidine compound of the formula I

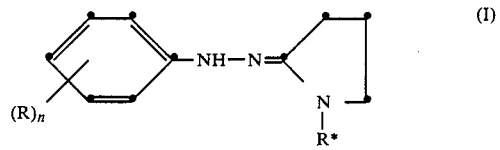

wherein
R is halogen or $C_1$-$C_4$-alkyl,
n is zero, 1 or 2,
R* is the group —CH=N—$R_1$ or

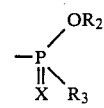

$R_1$ is a pyridine group which is bound by way of a carbon atom, and which is unsubstituted or substituted by a methyl group, or is a 2-thiazolyl group, and
$R_2$ is methyl or ethyl,
$R_3$ is $C_1$-$C_4$-alkyl, $C_1$-$C_2$-alkoxy or $C_1$-$C_4$-alkylthio, and
X is oxygen or sulfur,
including the acid addition salt of a compound of the formula I.

2. A compound of the formula I according to claim 1, in which R* is the group —CH=N—$R_1$, and R, $R_1$ and n have the meanings defined in claim 1.

3. A compound of the formula I according to claim 1, in which R* is the group

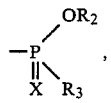

and R, $R_2$, $R_3$, X and n have the meanings defined in claim 1.

4. A compound of the formula I according to claim 2, in which R is chlorine and/or methyl, and n is 1 or 2, and $R_1$ has the meaning defined under the formula I.

5. A compound of the formula I according to claim 4, in which $(R)_n$ is 2,3-dichloro.

6. N-(2-[N'-(2',3'-Dichlorophenylhydrazono)-pyrrolidin-1-yl]-methylidene)-N-(6-methylpyridin-2-yl)-amine.

7. N-(2-[N'-(2',3'-Dichlorophenylhydrazono)-pyrrolidin-1-yl]-methylidene)-N-(3-methylpyridin-2-yl)-amine.

8. N-(2-[N'-(2',3'-Dichlorophenylhydrazono)-pyrrolidin-1-yl-methylidene)-N-(thiazol-2-yl)-amine.

9. An anti-parasitic composition which contains an effective amount of at least one compound of claim 1, together with an inert carrier.

10. A method of controlling parasites, which process comprises the application of an effective amount of a compound of claim 1 to a plant or animal host or the habitat thereof.

* * * * *